United States Patent [19]

Kemp

[11] Patent Number: 5,208,199
[45] Date of Patent: May 4, 1993

[54] CATALYST OF RARE EARTH AND PHOSPHORUS-CONTAINING XEROGELS FOR ALKOXYLATION PROCESS

[75] Inventor: Richard A. Kemp, Stafford, Tex.

[73] Assignee: Shell Oil Company, Houston, Tex.

[21] Appl. No.: 806,068

[22] Filed: Dec. 9, 1991

Related U.S. Application Data

[62] Division of Ser. No. 513,391, Apr. 23, 1990, Pat. No. 5,118,870.

[51] Int. Cl.$^5$ .................. B01J 23/10; B01J 27/18
[52] U.S. Cl. ................................................. 502/208
[58] Field of Search .................. 502/208; 423/263

[56] References Cited

U.S. PATENT DOCUMENTS

| | | | |
|---|---|---|---|
| 4,098,818 | 7/1978 | Krummel et al. | 260/535 R |
| 4,210,764 | 7/1980 | Yang et al. | 568/618 |
| 4,223,164 | 9/1980 | Yang et al. | 568/618 |
| 4,239,917 | 12/1980 | Yang | 568/618 |
| 4,302,613 | 11/1981 | Yang et al. | 568/618 |
| 4,306,093 | 12/1981 | Yang et al. | 568/618 |
| 4,375,564 | 3/1983 | Edwards | 568/618 |
| 4,453,022 | 6/1984 | McCain et al. | 568/618 |
| 4,453,023 | 6/1984 | McCain et al. | 568/618 |
| 4,456,697 | 6/1984 | Yang | 502/171 |
| 4,481,302 | 11/1984 | McDaniel et al. | 502/150 |
| 4,483,941 | 11/1984 | Yang | 502/171 |
| 4,665,236 | 5/1987 | Edwards | 568/618 |
| 4,689,435 | 8/1987 | Edwards | 568/618 |
| 4,721,816 | 1/1988 | Edwards | 568/618 |
| 4,721,817 | 1/1988 | Edwards | 518/618 |
| 4,727,199 | 2/1988 | King | 568/620 |

FOREIGN PATENT DOCUMENTS

| | | |
|---|---|---|
| 026544 | 9/1980 | European Pat. Off. . |
| 026546 | 9/1980 | European Pat. Off. . |
| 026547 | 9/1980 | European Pat. Off. . |
| 250168 | 6/1987 | European Pat. Off. . |
| 52-051307 | 10/1975 | Japan . |
| 1462134 | 3/1975 | United Kingdom . |
| 1553561 | 7/1976 | United Kingdom . |

*Primary Examiner*—W. J. Shine
*Attorney, Agent, or Firm*—Pamela J. McCollough

[57] ABSTRACT

Alkylene oxide adducts of organic compounds having active hydrogen atoms are prepared by a process which comprises contacting and reacting an alkylene oxide reactant comprising one or more vicinal alkylene oxides with an active hydrogen containing reactant comprising one or more compounds having active hydrogen atoms in the presence of a catalytically effective amount of a xerogel comprising one or more compounds comprising a rare earth element and phosphorus. The product alkoxylates are known to be useful, for instance, as nonionic surfactants, wetting and emulsifying agents, solvents, and chemical intermediates.

14 Claims, No Drawings

CATALYST OF RARE EARTH AND PHOSPHORUS-CONTAINING XEROGELS FOR ALKOXYLATION PROCESS

This is a division, of application Ser. No. 07/513,391, filed Apr. 23, 1990, now U.S. Pat. No. 5,118,870.

FIELD OF THE INVENTION

This invention relates to an alkoxylation process in which alkylene oxides are reacted with compounds having active hydrogen atoms in the presence of a catalyst comprising a xerogel comprising one or more compounds of a rare earth element and phosphorus. In particularly preferred embodiments, the invention relates to processes for the preparation of alkoxylate products useful as nonionic surfactants.

BACKGROUND OF THE INVENTION

A large variety of products useful, for instance, as nonionic surfactants, wetting and emulsifying agents, solvents, and chemical intermediates, are prepared by the addition reaction (alkoxylation reaction) of alkylene oxides (epoxides) with organic compounds having one or more active hydrogen atoms. For example, particular mention may be made of the alkanol ethoxylates and alkyl-substituted phenol ethoxylates prepared by the reaction of ethylene oxide with aliphatic alcohols or substituted phenols of about 6 to 30 carbon atoms. Such ethoxylates, and to a lesser extent corresponding propoxylates and compounds containing mixed oxyethylene and oxypropylene groups, are widely employed as nonionic detergent components of commercial cleaning formulations for use in industry and in the home. As another example, the addition reaction of propylene oxide with polyols provides intermediates for the preparation of polyurethane products.

An illustration of the preparation of an alkanol ethoxylate (represented by formula III below) by addition of a number (n) of ethylene oxide molecules (formula 11) to a single alkanol molecule (formula 1) is presented by the equation

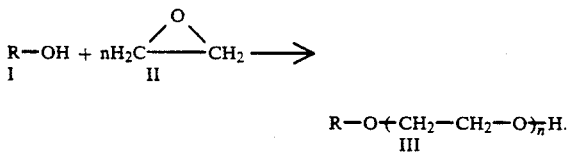

$$R-O(CH_2-CH_2-O)_nH.$$
III

The addition of alkylene oxides to alcohols and other active hydrogen containing compounds is known to be desirably promoted by a catalyst which is in conventional practice either basic or acidic in character. Recognized in the art as suitable basic catalysts are the basic compounds of the alkali metals of Group I of the Periodic Table, e.g., sodium, potassium, rubidium, and cesium, and the basic salts of certain of the alkaline earth metals of Group II of the Periodic Table, e.g., calcium, strontium, barium and in some cases magnesium. Conventional acidic alkoxylation catalysts include, broadly, Lewis acid or Friedel-Crafts catalysts. Specific examples of these acid catalysts are the fluorides, chlorides, and bromides of boron, antimony, tungsten, iron, nickel, zinc, tin, aluminum, titanium and molybdenum. The use of complexes of such halides with, for example, alcohols, ethers, carboxylic acids, and amines has also been reported. Still other examples of known acidic alkoxylation catalysts are sulfuric and phosphoric acids; perchloric acid and the perchlorates of magnesium, calcium, manganese, nickel and zinc.. certain metal oxalates, sulfates, phosphates, carboxylates and acetates; alkali metal fluoroborates; zinc titanate, and certain metal salts of benzene sulfonic acid.

Other art on the subject of alkoxylation includes U.S. Pat. No. 4,727,199, which describes a process for reacting a liquid or solid alkylene oxide with a liquid or gaseous active hydrogen compound, in the presence of a catalytic amount of an anion-bound metal oxide heterogenous catalyst, wherein the anion is $SO_4$, $BF_4$, $CO_3$, $BO_3$, $PO_4$, $SeO_4$, $MoO_4$, $B_4O_7$ or $PF_6$ and the metal oxide is an oxide of zirconium, nickel, aluminum, tin, calcium, magnesium, iron, titanium, thorium, hafnium, or rubidium. Still other prior art describes the use of zeolitic materials as alkoxylation catalysts, while European patent application 0250168 and other art cited therein disclose lamellar clay catalysts.

Alkylene oxide addition reactions are known to produce a product mixture of various alkoxylate molecules having different numbers of alkylene oxide adducts (oxyalkylene adducts), e.g., having different values for the adduct number n in formula 111 above. The adduct number is a factor which in many respects controls the properties of the alkoxylate molecule, and efforts are made to tailor the average adduct number of a product and/or the distribution of adduct numbers within a product to the product's intended service. In certain preferred embodiments, the present invention provides a process characterized by enhanced selectivity for the preparation of alkoxylate mixtures in which a relatively large proportion of the alkoxylate molecules have a number (n) of alkylene oxide adducts that is within a relatively narrow range of values.

It is known in the art that alcohol alkoxylate products having a narrow range alkylene oxide adduct distribution are preferred for use in certain detergent formulations (Great Britain Patent No. 1 462, 134. Derwent Publications Research Disclosure number 194.010). Narrow-range alcohol alkoxylates are also known to be particularly valuable as chemical intermediates in the synthesis of certain carboxyalkylated alkyl polyethers (U.S. Pat. No. 4,098,818) and of certain alkyl ether sulfates (Great Britain Pat. No. 1,553,561). Conventional commercial alkoxylate preparation, which has in large part been limited to the use of basic catalysts, particularly the metals sodium and potassium and their oxides and hydroxides, yields only a relatively broad distribution range product. Conventional acid-catalyzed alkoxylation reactions have long been known to produce a more narrow range product than that obtained with the alkali metal catalysts. However, acid catalysts have substantial disadvantages in several other respects. For instance, the acids are often unstable with limited life and effectiveness as catalysts in the alkoxylation mixture. Both the acid catalysts themselves and their decomposition products catalyze side reactions producing relatively large amounts of polyalkylene glycols, and also react directly with the components of the alkoxylation mixture to yield undesirable, and often unacceptable, by-products such as organic derivatives of the acids.

Also of substantial importance in alkoxylation processes is the ability of the process to minimize the quantity of unreacted (or residual) active hydrogen reactant remaining in the final product. A high level of residual reactant either represents a loss of valuable reactant, or requires that further processing of the product be carried out to recover the reactant. Moreover, the presence of the unreacted material is often a disadvantage from the standpoint of product quality and environmental concerns. For instance, residual alkanol in a detergent alcohol ethoxylate product contributes to volatile organic emissions during spray drying of detergent formulations.

It has recently been reported in the art that, in addition to conventional acidic catalysts, a number of other substances have been found to function as catalysts or in co-catalyst combinations which are capable of producing relatively narrow distributions for the oxyalkylene adducts of higher alkanols and other active hydrogen containing compounds. For instance, it has recently been disclosed (U.S. Pat. Nos. 4,306,093 and 4,239,917, and published European Patent Application Nos. 0026544, 0026546, 0026547) that certain compounds of barium, strontium, and calcium promote narrow-range alkoxylation products. U.S. Pat. Nos. 4,210,764 and 4,223,164 describe the use of cresylic acids to promote alkoxylation catalyzed by barium and strontium compounds. U.S. Pat. No. 4,302,613 discloses that a more peaked reaction product can be obtained by combining barium and strontium alkoxylation catalysts with co-catalysts such as calcium oxide, calcium carbide, calcium hydroxide, magnesium metal, magnesium hydroxide, zinc oxide and aluminum metal. U.S. Pat. No. 4,453,023 describes a process for preparing alkoxylates having a narrower molecular weight distribution which employs a catalyst comprising a barium compound and a promoter selected from the class consisting of super-phosphoric acid, phosphoric acid, diphosphoric acid, triphosphoric acid, phosphorous acid, dihydrogen phosphate compounds, oxides of phosphorus, carbon dioxide, and oxalic acid. U.S. Pat. No. 4,453,022 describes a similar process wherein the catalyst comprises a calcium or strontium compound and a promoter selected from the class consisting of super-phosphoric acid, phosphoric acid, diphosphoric acid, triphosphoric acid, phosphorous acid, dihydrogen phosphate compounds, oxides of phosphorus, sulfuric acid, bisulfate compounds, carbonic acid, bicarbonate compounds, carbon dioxide, oxalic acid and oxalic acid salts, sulfur trioxide, sulfur dioxide, and sulfurous acid. Published PCT application WO 85/00365 discloses other activated calcium containing alkoxylation catalysts capable of producing narrow range alkoxylation products. U.S. Pat. No. 4,375,564 reports that a narrow range product results from alkoxylation reactions catalyzed by a magnesium compound in combination with a compound of one of the elements aluminum, boron, zinc, titanium, silicon, molybdenum, vanadium, gallium, germanium, yttrium, zirconium, niobium, cadmium, indium, tin, antimony, tungsten, hafnium, tantalum, thallium, lead and bismuth. U.S. Pat. No. 4,483,941 discloses catalysts for alkoxylation reactions which comprise either $BF_3$ or $SiF_4$ in combination with an alkyl or alkoxide compound of aluminum, gallium, indium, thallium, titanium, zirconium, and hafnium. U.S. Pat. No. 4,456,697 describes an alkoxylation catalyst which comprises a mixture of HF and one or more metal alkoxides. Japanese patent specification 52051307 to Tokuyama Soda KK discloses the selective preparation of mono- rather than di- or tri-alkylene glycol esters from alkylene oxide and alcohol using solid acid catalysts such as silica, alumina, titania, vanadium pentoxide, antimony pentoxide, titanyl sulfate, tungstic acid, phosphotungstic acid, and silver perchlorite.

Recently issued U.S. Pat. No. 4,721,816 claims a process for preparing narrow range distribution alkoxylates, wherein the catalyst is a combination of one or more sulfur-containing acids with one or more aluminum alcoholate or phenolate compounds. U.S. Pat. No. 4,721,817 claims a similar process wherein the combination contains one or more phosphorus-containing acids.

U.S. Pat. Nos. 4,665,236 and 4,689,435 describe a process for the alkoxylation of active hydrogen reactants using certain bimetallic oxo catalysts. The catalysts described in U.S. Pat. No. 4,665,236 include compounds in which one of the metal species in the bimetallic molecule is lanthanum, and European application 0250168 discloses lamellar clay catalysts which have been ion exchanged with lanthanum and other rare earth elements.

The alkoxylation catalysts in the references discussed above are prepared by conventional methods such as simple chemical reactions, i.e.. acid-base or metathesis reactions, or methods known in the art such as ion exchange.

It has now been found that hydrogel-derived xerogels comprising one or more compounds comprising a rare earth element and phosphorus are effective catalysts for the addition reaction of alkylene oxides with organic compounds having active hydrogen atoms. It has further been found that, in certain preferred embodiments, an alkoxylation reaction catalyzed by a xerogel comprising one or more compounds comprising a rare earth element and phosphorus provides an alkoxylate product, particularly an alkanol ethoxylate product, of exceptionally narrow-range alkylene oxide adduct distribution.

SUMMARY OF THE INVENTION

The present invention is particularly directed to a process for the preparation of alkoxylates of active hydrogen containing organic compounds which comprises contacting an alkylene oxide reactant comprising one or more vicinal alkylene oxides with an active hydrogen reactant comprising one or more organic compounds (e.g., alcohols, phenols, thiols, amines, polyols, carboxylic acids, etc.) having one or more active hydrogen atoms, in the presence of a catalytically effective amount of a xerogel comprising one or more compounds comprising a rare earth element and phosphorus.

As used herein, the term "rare earth" elements are those elements of atomic numbers 57 through 71. The terms "rare earth element" and "lanthanide" are used interchangeably in the present specification.

As used herein, the term "xerogel" refers to the product obtained by drying hydrogels whereby the structure is for the most part irreversibly set. While xerogels may contain a residuum of water, i.e., as much as 75% by weight, they are usually encountered as spray dried powders containing 65-99% solids and are considered to be rigid solids. As used herein, the term "hydrogel" refers to gels, precipitated gels, hydrous oxide precipitates, or combinations thereof in an undried state. Water is a major component of these materials as formed, comprising 80% to 95% of their weight. The water is held within the pores or interstices of the semi-rigid hydrogel.

DESCRIPTION OF THE PREFERRED EMBODIMENTS

The present invention centers upon discoveries associated with the use in an alkoxylation process of a certain class of catalysts. Apart from the use of such catalysts, the process of the invention is, as a general rule, suitably conducted using such reactants and practicing under such processing procedures and reaction conditions as are well known to the art for alkoxylation reactions. Certain preferences may, however, be expressed for particular reactants, procedures and conditions.

Thus, for instance, the invention is preferably applied to processes utilizing an alkylene oxide (epoxide) reactant which comprises one or more vicinal alkylene oxides, particularly the lower alkylene oxides and more particularly those in the $C_2$ to $C_4$ range. In general, the alkylene oxides are represented by the formula

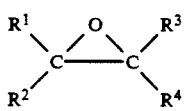

wherein each of the $R^1$, $R^2$, $R^3$ and $R^4$ moieties is individually selected from the group consisting of hydrogen and alkyl moieties. Reactants which comprise ethylene oxide, propylene oxide, or mixtures of ethylene oxide and propylene oxide are more preferred, particularly those which consist essentially of ethylene oxide and propylene oxide. Alkylene oxide reactants consisting essentially of ethylene oxide are considered most preferred from the standpoint of commercial opportunities for the practice of alkoxylation processes, and also from the standpoint of the preparation of products having narrow-range ethylene oxide adduct distributions.

Likewise, the active hydrogen reactants suitably utilized in the process of the invention include those known in the art for reaction with alkylene oxides and conversion to alkoxylate products. Suitable classes of active hydrogen reactants include (but are not necessarily limited to) alcohols, phenols, thiols (mercaptans), amines, polyols, carboxylic acids, and mixtures thereof. Preference generally exists for use of hydroxyl-containing reactants. More preferably, the active hydrogen containing reactant consists essentially of one or more active hydrogen containing compounds selected from the group consisting of alkanols, alkyl polyols and phenols (including alkyl-substituted phenols).

Among the suitable carboxylic acids, particular mention may be made of the mono- and dicarboxylic acids, both aliphatic (saturated and unsaturated) and aromatic. Specific examples include acetic acid, propionic acid, butyric acid, valeric acid, caproic acid, lauric acid, myristic acid, palmitic acid, stearic acid, oleic acid, rosin acids, tall oil acids, terephthalic acid, benzoic acid, phenylacetic acid, toluic acid, acrylic acid, methacrylic acid, crotonic acid, maleic acid, and the like.

Among the suitable amines, particular mention may be made of primary, secondary and tertiary alkylamines and of alkylamines containing both amino and hydroxyl groups. e.g., N,N-di(n-butyl)-ethanolamine and tripropanolamine.

Among the suitable thiols, particular mention may be made of primary, secondary and tertiary alkane thiols having from 1 to about 30 carbon atoms, particularly those having from about 8 to 20 carbon atoms. Specific examples of suitable tertiary thiols are those having a highly branched carbon chain which are derived via hydrosulfurization of the products of the oligomerization of lower olefins, particularly the dimers, trimers, and tetramers and pentamers of propylene and the butylenes. Secondary thiols are exemplified by the lower alkane thiols, such as 2-propanethiol, 2-butanethiol, and 3-pentanethiols, as well as by the products of the hydrosulfurization of the substantially linear oligomers of ethylene as are produced by the Oxo process. Representative but not limiting examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol, and 8-octadencanethiol, and the branched carbon chain products, such as 2-methyl-4-tridecanethiol. Primary thiols are typically prepared from terminal olefins by hydrosulfurization under free-radical conditions and include, for example. 1-butanethiol, 1-hexane-thiol, 1-dodecanethiol, 1-tetradecanethiol and 2-methyl-1-tridecanethiol.

Among the polyols, particular mention may be made of those having from 2 to about 6 hydroxyl groups. Specific examples include the alkylene glycols such as ethylene glycol, propylene glycol, hexylene glycol, and decylene glycol, the polyalkylene glycol ethers, such as diethylene glycol. triethylene glycol, propylene glycol, dipropylene glycol, tripropylene glycol, glycerine, sorbitol, and the like.

The alcohols (both mono- and poly-hydroxy) and the phenols (including alkyl-substituted phenols) are preferred classes of active hydrogen reactants for purposes of the invention. Among the phenols, particular mention may be made of phenol and of alkyl-substituted phenols wherein each alkyl substituent has from one to about 30 (preferably from one to about 20) carbon atoms, for example, p-methylphenol, p-ethylphenol, p-hexylphenol, nonylphenol, p-decylphenol, didecyl phenol and the like.

Acyclic aliphatic mono-hydric alcohols (alkanols) form a most preferred class of reactants, particularly the primary alkanols, although secondary and tertiary alkanols are also very suitably utilized in the process of the invention. Preference can also be expressed, for reason of both process performance and commercial value of the product, for alkanols having from one to about 30 carbon atoms, with $C_6$ to $C_{24}$ alkanols considered more preferred and $C_8$ to $C_{20}$ alkanols considered most preferred. As a general rule, the alkanols may be of branched or straight chain structure, although preference further exists for alkanol reactants in which greater than about 50 percent, more preferably greater than about 60 percent, and most preferably greater than about 70 percent of the molecules are of linear (straight-chain) carbon structure.

The general suitability of such alkanols as reactants in alkoxylation reactions is well recognized in the art. Commercially available mixtures of primary monohydric alkanols prepared via the oligomerization of ethylene and the hydroformylation or oxidation and hydrolysis of the resulting higher olefins are particularly preferred. Examples of commercially available alkanol mixtures include the NEODOL Alcohols, trademark of and sold by Shell Chemical Company, including mixtures of $C_9$, $C_{10}$ and $C_{11}$ alkanols, (NEODOL 91 Alcohol). mixtures of $C_{12}$ and $C_{13}$ alkanols (NEODOL 23 Alcohol). mixtures of $C_{12}$, $C_{13}$, $C_{14}$, and $C_{15}$ alkanols (NEODOL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418); and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Procter and Gamble Company and the TA alcohols of Ashland Oil Company.

Among the polyols, particular mention may be made of those having from 2 to about 6 hydroxyl groups and 2 or more, preferably 2 to 30 carbon atoms. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like. Higher oligomers and polymers of the polyols are also very suitable.

The active hydrogen containing reactant is also very suitably the alkoxylate product of a previous alkoxylation of an active hydrogen containing compound.

Further examples of both specific alkylene oxide reactants and specific active hydrogen containing reactants suitable for use in this invention are recited in the aforementioned U.S. Patents, the relevant disclosures of which are incorporated herein by this reference.

The alkylene oxide reactant and the active hydrogen reactant are contacted in the presence of a xerogel comprising one or more compounds of a rare earth element and phosphorus. The compound(s) comprising a rare earth element and phosphorus is selected from the group consisting of lanthanum phosphate, cerium phosphate, neodymium phosphate, samarium phosphate, gadolinium phosphate, dysprosium phosphate and mixtures thereof. The rare earth/phosphorus xerogel catalysts of the present invention are derived from hydrogels and can be prepared by coprecipitation of a rare earth or lanthanide compound, a phosphorus compound and a basic compound in an aqueous solution.

In a preferred embodiment, the xerogels, are prepared by coprecipitating one or more rare earth or lanthanide compounds, a phosphorus compound and a basic compound in an aqueous solution. Suitable lanthanide compounds for use in the coprecipitation of the hydrogel include lanthanide chloride in the hydrated form, lanthanide nitrate and lanthanide carbonate, with lanthanide chloride in the hydrated form being preferred. Suitable phosphorus compounds include sodium phosphate, potassium phosphate and ammonium potassium phosphate, with sodium phosphate being preferred. Suitable basic compounds include sodium hydroxide, ammonium hydroxide, potassium hydroxide and cesium hydroxide, with sodium hydroxide being preferred. The precipitation is typically carried out at a temperature in the range of from about 5° C to about 95° C, preferably from about 20° C to about 40° C. The length of time required for precipitation is typically from about 1 minute to about 1 hour. The period of time for the precipitation should be sufficiently long for adequate mixing of the materials so that a relatively stable pH is maintained.

After precipitation of rare earth/phosphorus-containing hydrogel, the hydrogel is subjected to stirring for at least about 30 minutes in order to allow complete reaction to occur. Thereafter, the hydrogel is filtered in routine fashion and washed to remove substantially all of the water-soluble salts formed during the precipitation of the hydrogel. The preferred solvent for washing is water although other solvents such as lower alkanols may be used.

The rare earth/phosphorus-containing hydrogel is then subjected to drying to form a xerogel. The extent to which water is removed from the hydrogel during drying will vary widely depending upon the solids content of the hydrogel and the nature of the drying operation conducted. Drying may be carried out using conventional means such as air drying, vacuum, drying, forced draft drying or similar means. Drying temperatures are not critical and depend upon the particular means utilized for drying and the extent to which drying of the hydrogel is desired. Drying will typically be carried out at temperatures in the range of from about 80° C. to about 300° C. It is to be understood that drying of the hydrogel does not have to be complete and further drying can result in further removal of water.

In a preferred embodiment, the catalysts in the present invention contain from about 70 percent by weight to about 99 percent by weight, preferably from about 80 percent by weight to about 95 percent by weight solids as determined by thermogravimetric analysis.

The rare earth/phosphorus xerogel catalysts thus prepared typically contain from about 40 percent by weight to about 75 percent by weight, preferably from about 50 percent by weight to about 70 percent by weight, basis total catalyst, of rare earth element, and from about 8 percent by weight to about 15 percent by weight, preferably from about 10 percent by weight to about 13 percent by weight, basis total catalyst, of phosphorus.

In addition, the catalyst may also suitably contain other substances, including those which may be introduced into the process as impurities as well as those which may be added to promote or modify catalyst activity.

The xerogel comprising one of more compounds comprising a rare earth element and phosphorus is present in the reaction mixture in a catalytically effective amount, i.e., an amount sufficient to promote the alkoxylation reaction or influence the alkoxylene oxide adduct distribution of the product. In a preferred embodiment, the catalyst is used in amount between about 0.1 percent by weight and about 10 percent by weight, preferably between about 0.5 percent by weight and about 3 percent by weight, basis starting weight of active hydrogen reactant to be ethoxylated. As a general rule, the higher the desired average alkylene oxide adduct number of the product and the higher the desired reaction rate, the greater the required quantity of catalyst.

In a preferred embodiment, the invention is a process which comprises contacting and reacting an alkylene oxide reactant (particularly a reactant comprising ethylene oxide, propylene oxide, or a mixture of propylene oxide and ethylene oxide) with an active hydrogen containing reactant (particularly an alcohol, polyol, or other hydroxyl containing compound), in the presence of a xerogel comprising one or more compounds comprising lanthanum and phosphorus wherein the catalyst contains from about 40 percent by weight to about 70 percent by weight, preferably from about 50 percent by weight to about 65 percent by weight, basis total catalyst, of lanthanum, and from about 8 percent by weight to about 13 percent by weight phosphorus, preferably from about 10 percent by weight to about 12 percent by weight, basis total catalyst, of phosphorus. In a most preferred embodiment, ethylene oxide is contacted with a $C_1$ to $C_{30}$ primary alkanol in the presence of a xerogel comprising lanthanum phosphate.

In terms of processing procedures, the alkoxylation reaction in the invention may be conducted in a generally conventional manner. The process can be carried out either batchwise or continuously, using a fixed bed catalyst, or a stirrer equipped reactor or other mobile catalyst contacting process as well as any other well known contacting technique. For example, the liquid active hydrogen reactant may initially be contacted with the catalyst. The catalyst and liquid reactant are contacted, preferably under agitation, with alkylene oxide reactant, which is typically introduced in gaseous form, at least for the lower alkylene oxides. The order in which the reactants and catalyst are contacted has not been found to be critical to the invention.

Overall, the two reactants are utilized in quantities which are predetermined to yield an alkoxylate product of the desired mean or average adduct number. The average adduct number of the product is not critical to this process. Such products commonly have an average adduct number in the range from less than one to about 30 or greater.

In general terms, suitable and preferred process temperatures and pressures for purposes of this invention are the same as in conventional alkoxylation reactions between the same reactants, employing conventional catalysts. A temperature of at least about 90° C., particularly at least about 120° C. and most particularly at least about 130° C., is typically preferred from the standpoint of the rate of reaction, while a temperature less than about 250° C., particularly less than about 210° C., and most particularly less than about 190° C., is typically desirable to minimize degradation of the product. As is known in the art, the process temperature can be optimized for given reactants, taking such factors into account.

Super-atmospheric pressures, e.g., pressures between about 10 and 150 psig, are preferred, with pressure being sufficient to maintain the active hydrogen reactant substantially in the liquid state.

When the active hydrogen reactant is a liquid and the alkylene oxide reactant is a vapor, alkoxylation is then suitably conducted by introducing alkylene oxide into a pressure reactor containing the liquid active hydrogen reactant and the catalyst. For considerations of process safety, the partial pressure of a lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig, is considered more preferred.

The time required to complete a process according to the invention is dependent both upon the degree of alkoxylation that is desired (i.e.. upon the average alkylene oxide adduct number of the product) as well as upon the rate of the alkoxylation reaction (which is, in turn dependent upon temperature, catalyst quantity and nature of the reactants). A typical reaction time for preferred embodiments is in the range from 1 to 24 hours.

After the ethoxylation reaction has been completed, the product is preferably cooled. If desired, catalyst can be removed from the final product, although catalyst removal is not necessary to the process of the instant invention. Any catalyst residues may be removed, for example, by filtration, precipitation, extraction, or the like.

The ranges and limitations procided in the instant specification and claims are those which are believed to particularly point out and distinctly claim the instant invention. It is, however, understood that other ranges and limitations that perform substantially the same function in substantially the same way to achieve the same or substantially the smae result are intended to be within the scope of the instant specification and claims.

The following Examples are provided to further illustrate certain specific aspects of the invention but are not intended to limit its broader scope.

EXAMPLE 1

A lanthanum phosphate xerogel was prepared by the following procedure. Lanthanum chloride heptahydrate (15 grams, 40 mmoles) was dissolved in 50 ml of deionized water, as were sodium hydroxide (3.2 grams, 80 mmoles) in 50 ml of water and tribasic sodium phosphate dodecahydrate (5.07 grams. 16.7 mmoles) in 50 ml of deionized water. Deionized water (350 ml) served as a heel for the precipitation. All three solutions were added simultaneously in a dropwise fashion to the heel, maintaining a near neutral pH. The slurry was stirred at ambient temperature for 30 minutes, filtered through a medium porosity frit, washed with 200 ml of deionized water, and partially dried on the frit by pulling air through the frit. The material was dried further at 120° C. under a rough (100 mm) vacuum for several hours. The resulting material was 67% by weight lanthanum.

An alkoxylation process in accordance with the invention was conducted under the following procedures. The alkylene oxide reactant for this process embodiment consisted of ethylene oxide and the active hydrogen (20% branched), alkanols having twelve and thirteen carbon atoms (about 40% by mol $C_{12}$ and 60% by mol $C_{13}$).

Initially, 2.0 grams of the powder prepared as described above was added to 110 grams of NEODOL 23 Alcohol, and the mixture was heated in a 500 milliliter autoclave to 140° C. under nitrogen sparge to drive off water. A mixture of nitrogen and ethylene oxide was then introduced into the reactor to a total pressure of 60 psia (30 psia nitrogen and 30 psia ethylene oxide). Alkoxylation (ethoxylation) commenced immediately. Additional ethylene oxide was supplied on demand to maintain an essentially constant 60 psia pressure Temperature was maintained at 140° C. A total of 161 grams of ethylene oxide was taken up over a period of 6 hours. The reactor was maintained for an additional 1 hour to consume unreacted ethylene oxide in the system.

The product was analyzed by GC-LC techniques and found to have a mean average adduct number of 5.8. The ethylene oxide adduct distribution of the product is presented in the following table. The only observed by-products were polyethylene glycols (PEG).

| ETHOXYLATE DISTRIBUTION | |
|---|---|
| Adduct Number | Concentration |
| 0 (Residual Alcohol) | 2.9% wt |
| 1 | 1.1 |
| 2 | 1.8 |
| 3 | 4.5 |
| 4 | 9.4 |
| 5 | 15.2 |
| 6 | 17.8 |
| 7 | 15.8 |
| 8 | 11.5 |
| 9 | 7.4 |
| 10 | 4.5 |
| 11 | 2.7 |
| 12 | 1.7 |
| 13 | 1.1 |
| 14 | 0.7 |
| 15 | 0.5 |

EXAMPLE 2

A lanthanum phosphate xerogel was prepared by the following procedure. Lanthanum chloride heptahydrate (15 grams, 40 mmoles) was dissolved in 50 ml of deionized water, as were sodium hydroxide (1.6 grams, 40 mmoles) in 50 ml of water and tribasic sodium phosphate dodecahydrate (10.14 grams, 33.4 mmoles) in 50 ml of deionized water. Deionized water (350 ml) served as a heel for the precipitation. All three solutions were added simultaneously in a dropwise fashion to the heel, maintaining a near neutral pH. The slurry was stirred at ambient temperature for 30 minutes, filtered through a medium porosity frit, washed with 200 ml of deionized water, and partially dried on the frit by pulling air through the frit. The material was dried further at 120° C. under a rough (100 mm) vacuum for several hours. The resulting material was 63% by weight lanthanum.

Two grams of this powder was added to 110 grams of the NEODOL 23 Alcohol in a 500 milliliter autoclave, and the temperature of the mixture was ramped to 140° C. under nitrogen sparge to drive off water. The alcohol was ethoxylated at 140° C. and at a pressure of 60 psia (30 psia ethylene oxide and 30 psia nitrogen). A total of 202 grams of ethylene oxide was consumed over a period of 2.5 hours, yielding a product having a mean average adduct number of 7.8. The adduct distribution of this product is presented in the following table.

| ETHOXYLATE DISTRIBUTION | |
|---|---|
| Adduct Number | Concentration |
| 0 (Residual Alcohol) | 1.2% wt |
| 1 | 0.5 |
| 2 | 0.5 |
| 3 | 0.5 |
| 4 | 2.0 |
| 5 | 7.7 |
| 6 | 17.5 |
| 7 | 22.9 |
| 8 | 18.8 |
| 9 | 11.5 |

| ETHOXYLATE DISTRIBUTION | |
|---|---|
| Adduct Number | Concentration |
| 10 | 6.2 |
| 11 | 3.4 |
| 12 | 2.1 |
| 13 | 1.5 |
| 14 | 1.0 |
| 15 | 0.8 |

EXAMPLE 3

A lanthanum phosphate xerogel was prepared by the following procedure. Lanthanum chloride heptahydrate (15 grams, 40 mmoles) was dissolved in 50 ml of deionized water, as was tribasic sodium phosphate dodecahydrate (15.2 grams, 40 mmoles) in 50 ml of deionized water. Deionized water (350 ml) served as a heel for the precipitation. Both solutions were added simultaneously in a dropwise fashion to the heel, maintaining a near neutral pH. The slurry was stirred at ambient temperature for 30 minutes, filtered through a medium porosity frit, washed with 200 ml of deionized water, and partially dried on the frit by pulling air through the frit. The material was dried further at 120° C. under a rough (100 mm) vacuum for several hours. The resulting material was 58% by weight lanthanum.

Two grams of this powder was added to 110 grams of NEODOL 23 Alcohol. An ethoxylation reaction was then carried out according to the procedures described in Example 2. A total of 200 grams of ethylene oxide was consumed over a 2.5 hour period at a reaction temperature of 140° C. The product had a mean average adduct number of 6.5. The adduct distribution of this product is presented in the following table.

| ETHOXYLATE DISTRIBUTION | |
|---|---|
| Adduct Number | Concentration |
| 0 (Residual Alcohol) | 2.3% wt |
| 1 | 0.8 |
| 2 | 0.7 |
| 3 | 1.5 |
| 4 | 4.3 |
| 5 | 11.3 |
| 6 | 19.2 |
| 7 | 20.8 |
| 8 | 15.5 |
| 9 | 9.3 |
| 10 | 5.2 |
| 11 | 2.9 |
| 12 | 1.8 |
| 13 | 1.2 |
| 14 | 0.8 |
| 15 | 0.7 |

What is claimed is:

1. A catalyst composition for the preparation of alkylene oxide adducts of active hydrogen-containing compounds consisting essentially of a xerogel consisting essentially of one or more compounds of a rare earth element and phosphorus.

2. The catalyst of claim 1 wherein said compound(s) of a rare earth element and phosphorus is selected from the group consisting of lanthanum phosphate, cerium phosphate, neodymium phosphate, samarium phosphate, gadolinium phosphate, dysprosium phosphate and mixtures thereof.

3. The catalyst of claim 2 wherein said compound(s) of a rear earth element and phosphorus is lanthanum phosphate.

4. The catalyst of claim 1 wherein said xerogel contains from about 40 percent by weight to about 75 percent by weight rare earth element and from about 8 percent by weight to about 15 percent by weight phosphorus.

5. The catalyst of claim 4 wherein said xerogel contains from about 50 percent by weight to about 70 percent by weight rare earth element and from about 10 percent by weight to about 13 percent by weight phosphorus.

6. The catalyst of claim 1 wherein said xerogel contains about 70 percent by weight to about 99 percent by weight solids.

7. The catalyst of claim 6 wherein said xerogel contains about 80 percent by weight to about 95 percent by weight solids.

8. A catalyst composition consisting essentially a xerogel consisting essentially one or more compounds of a rare earth element and phosphorus.

9. The catalyst of claim 8 wherein said compound(s) of a rare earth element and phosphorus is selected from the group consisting of lanthanum phosphate, cerium phosphate, neodymium phosphate, samarium phosphate, gadolinium phosphate, dysprosium phosphate and mixtures thereof.

10. The catalyst of claim 9 wherein said compound(s) of a rare earth element and phosphorus is lanthanum phosphate.

11. The catalyst of claim 8 wherein said xerogel contains from about 40 percent by weight to about 75 percent by weight rare earth element and from about 8 percent by weight to about 15 percent by weight phosphorus.

12. The catalyst of claim 11 wherein said xerogel contains from about 50 percent by weight to about 70 percent by weight rare earth element and from about 10 percent by weight to about 13 percent by weight phosphorus.

13. The catalyst of claim 8 wherein said xerogel contains about 70 percent by weight to about 99 percent by weight solids.

14. The catalyst of claim 13 wherein said xerogel contains about 80 percent by weight to about 95 percent by weight solids.

* * * * *